(12) United States Patent
Kim et al.

(10) Patent No.: US 10,583,025 B2
(45) Date of Patent: Mar. 10, 2020

(54) WEARING MODULE AND MOTION ASSISTANCE APPARATUS INCLUDING THE SAME

(71) Applicants:Samsung Electronics Co., Ltd., Suwon-si, Gyeonggi-do (KR); Korea University of Technology and Education Industry University Cooperation Foundation, Cheonan-si, Chungcheongnam-do (KR)

(72) Inventors: Jeonghun Kim, Suwon-si (KR); Yong Jae Kim, Cheonan-si (KR); Deok Won Lee, Cheonan-si (KR)

(73) Assignees: Samsung Electronics Co., Ltd., Gyeonggi-do (KR); Korea University of Technology and Education Industry University Cooperation Foundation, Cheonan-Si (KR)

( * ) Notice: Subject to any disclaimer, the term of this patent is extended or adjusted under 35 U.S.C. 154(b) by 364 days.

(21) Appl. No.: 15/426,178

(22) Filed: Feb. 7, 2017

(65) Prior Publication Data

US 2018/0064570 A1 Mar. 8, 2018

(30) Foreign Application Priority Data

Sep. 7, 2016 (KR) ........................ 10-2016-0115060

(51) Int. Cl.
*A61F 5/01* (2006.01)
*A61H 3/00* (2006.01)
(Continued)

(52) U.S. Cl.
CPC .............. *A61F 5/0102* (2013.01); *A61F 2/68* (2013.01); *A61F 5/0111* (2013.01); *A61H 1/0237* (2013.01); *A61H 3/00* (2013.01); *A61H 3/008* (2013.01); *A61F 2002/701* (2013.01); *A61F 2005/0141* (2013.01);
(Continued)

(58) Field of Classification Search
CPC combination set(s) only.
See application file for complete search history.

(56) References Cited

U.S. PATENT DOCUMENTS 8,025,632 B2 9/2011 Einarsson
8,439,852 B2 5/2013 Ebihara et al.
(Continued)

FOREIGN PATENT DOCUMENTS

EP 1 138 351 A2 10/2001
JP 4112543 B2 7/2008
(Continued)

*Primary Examiner* — Yashita Sharma
(74) *Attorney, Agent, or Firm* — Harness, Dickey & Pierce, P.L.C.

(57) ABSTRACT

A wearing module and a motion assistance apparatus including the same is disclosed, wherein the wearing module may include a base frame having a predetermined curved form to cover a body portion of a user, the base frame formed by a rigid material, a middle frame connected to the base frame and formed by a flexible material, the middle frame disposed in a longitudinal direction perpendicular to the base frame, and a connecting member extended from both end portions of the base frame to cover an edge of the middle frame, and bent to correspond to a deformation of the middle frame.

13 Claims, 10 Drawing Sheets

(51) Int. Cl.
    *A61H 1/02*     (2006.01)
    *A61F 2/68*     (2006.01)
    *A61F 2/70*     (2006.01)

(52) U.S. Cl.
    CPC ............... *A61F 2005/0155* (2013.01); *A61H 2201/165* (2013.01); *A61H 2201/1642* (2013.01)

(56) References Cited

U.S. PATENT DOCUMENTS

| | | |
|---|---|---|
| 2013/0303950 A1 | 11/2013 | Angold et al. |
| 2017/0360645 A1* | 12/2017 | Sodeyama ............... A61H 3/00 |

FOREIGN PATENT DOCUMENTS

| | | |
|---|---|---|
| JP | 5876358 B2 | 3/2016 |
| KR | 10-2009-0025184 | 3/2009 |
| KR | 10-2010-0110084 | 10/2010 |
| KR | 10-1616263 B1 | 4/2016 |

\* cited by examiner

WEARING MODULE AND MOTION ASSISTANCE APPARATUS INCLUDING THE SAME

CROSS-REFERENCE TO RELATED APPLICATION

This application claims under 35 U.S.C. § 119 to Korean Patent Application No. 10-2016-0115060, filed on Sep. 7, 2016, in the Korean Intellectual Property Office, the entire contents of which are incorporated herein by reference in their entirety.

BACKGROUND

1. Field

At least one example embodiment relates to a wearing module and/or a motion assistance apparatus including the same.

2. Description of the Related Art

There being a number of rapidly aging societies, many people are experiencing inconvenience and/or pain from joint problems. Thus, there is a growing interest in motion assistance apparatuses that enable the elderly and/or patients having joint problems to walk with less effort. Furthermore, motion assistance apparatuses for intensifying muscular strength of human bodies may be useful for military purposes.

For example, a motion assistance apparatus may include a body frame connected at a bottom portion to a pelvis frame, and a femoral frame, calf frame, and foot frame, worn by a user to cover respectively a torso, pelvis, thigh, calf and foot, of the user. The pelvis frame and the femoral frame may be connected by a hip joint portion such that the pelvis frame and the femoral frame are rotatable. The femoral frame and the calf frame may be connected by a knee joint portion such that the femoral frame and the calf frame are rotatable. The calf frame and the foot frame may be connected by an ankle joint portion such that the calf frame and the foot frame are rotatable.

The motion assistance apparatus may be provided in an active joint structure including a hydraulic system or a driving motor that drives each hip joint portion in order to add strength to a leg of the user. For example, the motion assistance apparatus may include two motors for transmitting a rotation power to each hip joint portion.

SUMMARY

Some example embodiments relate to a wearing module.

In some example embodiments, the wearable module includes a base frame having a curved shape such that the base frame is configured to cover a body portion of a user, the base frame including a rigid material, the base frame including two end portions; a middle frame connected to the base frame and extending longitudinally in a first direction perpendicular to the base frame, the middle frame including a flexible material; and a connecting member extending in the first direction from the end portions of the base frame and connected to edges of the middle frame, the connecting member configured to bend in response to a deformation of the middle frame caused by pressure applied thereto.

Some example embodiments relate to a wearable module.

In some example embodiments, the wearable module includes a base frame having a curved shape such that the base frame is configured to cover a body portion of a user, the base frame including two end portions; a middle frame including a bottom portion, side portions and an upper portion, the bottom portion connected to the base frame, the side portions symmetrically extending from both sides from a center portion of the base frame, and the upper portion being at a top of the side portion; a connecting member extending from the end portions of the base frame to sequentially cover edges of the side portions and the upper portion; and a supporting member extending in a same direction as the middle frame, the supporting member configured to support a pressure applied to the middle frame.

Some example embodiments relate to a motion assistance apparatus.

In some example embodiments, the motion assistance apparatus includes a wearing module configured to cover a body portion of a user, the wearing module including a base frame having a curved shape, a middle frame extending from the base frame, a connecting member configured to cover the middle frame, and a supporting member extending in a same direction as the middle frame; a supporting module configured to rotate relative to the wearing module; a driving module configured to drive the supporting module; and a power transmitting member configured to transmit a power to the supporting module.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 1:
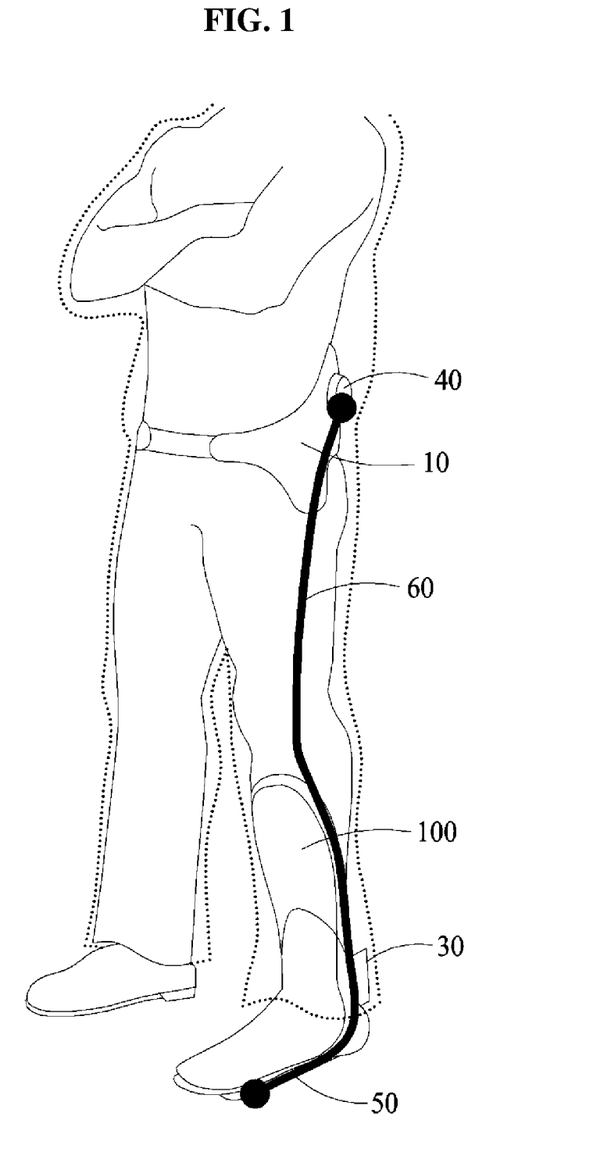
FIG. 1 illustrates a motion assistance apparatus being worn by a user according to at least one example embodiment.
Figure 2:
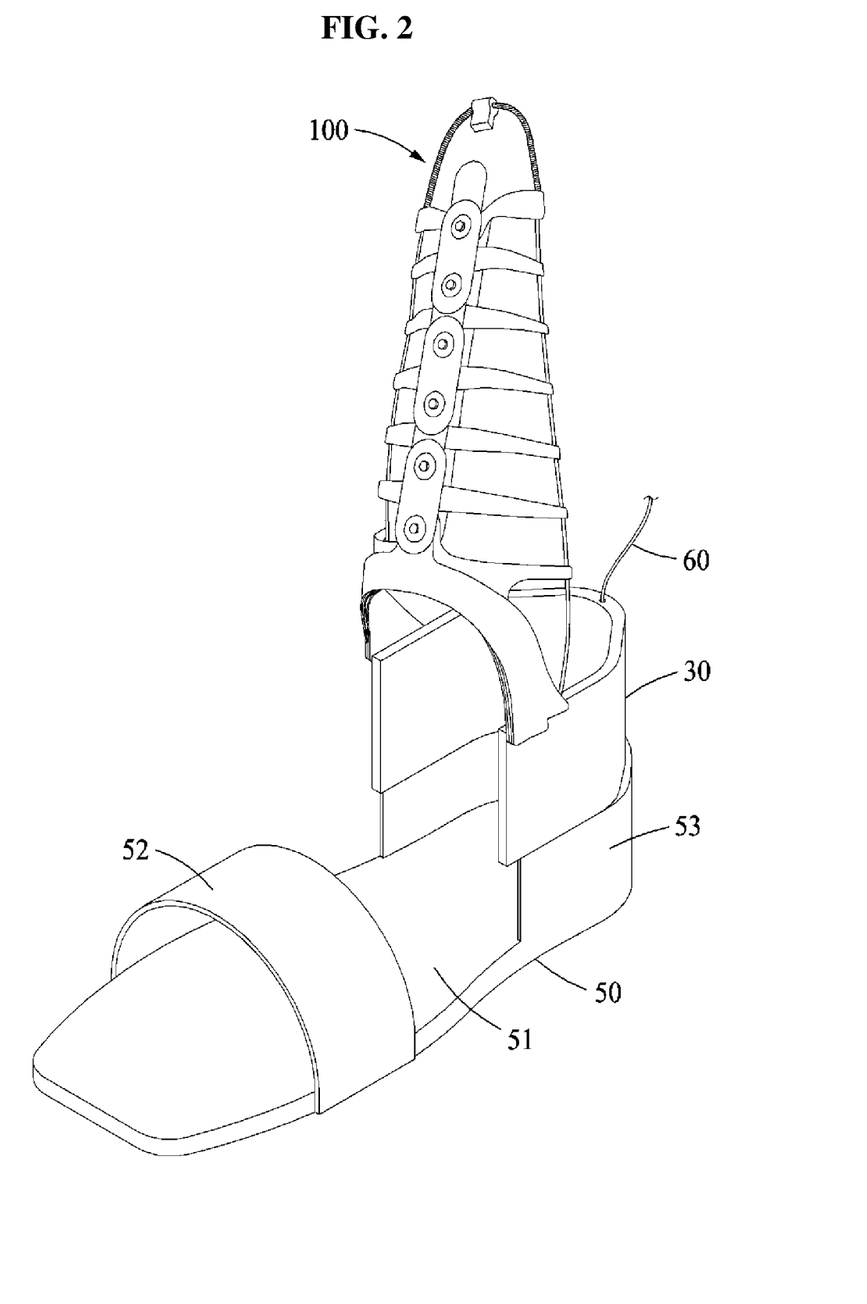
FIG. 2 is a perspective view illustrating a motion assistance apparatus according to at least one example embodiment.

FIG. 1 illustrates a motion assistance apparatus being worn by a user according to at least one example embodiment, and FIG. 2 is a perspective view illustrating the motion assistance apparatus according to at least one example embodiment.

Referring to FIGS. 1 and 2, a motion assistance apparatus may be worn by a user to assist a motion of the user. The user may be a human, an animal, or a robot. However, the user is not limited thereto. Although FIG. 1 illustrates a case in which the motion assistance apparatus assists a motion of an ankle joint of the user, the motion assistance apparatus may also assist a motion of another portion of the user, for example, a wrist joint, an elbow joint, and/or a knee joint. The motion assistance apparatus may assist a motion of a portion of the user. Hereinafter, a case in which the motion assistance apparatus assists a motion of an ankle joint of a human will be described. However, example embodiments are not limited thereto.

The motion assistance apparatus may include a waist wearable portion 10 disposed on a waist of the user, a wearing module 100, a driving module 40, a supporting module 50, a power transmitting member 60, and a connecting joint 30.

Referring to FIG. 2, the wearing module 100 may be attached to a first portion of the user, and configured to cover an external surface of the user. For example, the wearing module 100 may cover a shin of the user, and include a curved surface corresponding to a contact portion of the user.

The supporting module 50 may support a second portion of the user being adjacent to the first portion, and rotate with respect to the wearing module 100 using power transmitted from the power transmitting member 60. For example, the supporting module 50 may cover a portion of a sole of the user, a portion of an instep of the user, and/or a portion of an ankle of the user. For example, the supporting module 50 includes a sole pad 51 to support the sole, an instep supporter 52 to support the instep, and/or a connector 53 to connect the sole pad 51 and the connecting joint 30.

The driving module 40 may transmit a power to the supporting module 50. The driving module 40 may change a direction of movement of the power transmitting member 60, and include a clutch module to adjust a torque or a speed. The driving module 40 may be mounted at a position corresponding to a proximal part of the user. The proximal part of the user may be a center portion of the user, for example, a back, a waist or a torso.

For example, the driving module 40 may be disposed on the waist wearable portion 10. Compared to a case in which the driving module 40 is mounted on an end portion of the user, for example, a hand and a foot, the driving module 40 may decrease an amount of energy consumed by the user due to a weight of the driving module 40 when the driving module 40 is mounted on the waist wearable portion 10. Although not illustrated, the driving module 40 may be disposed on, for example, the wearing module 100, but a position of the driving module 40 is not limited thereto.

The power transmitting member 60 may transmit the power from the driving module 40 to the supporting module 50. For example, the power transmitting member 60 may be connected to the supporting module 50 by passing the power transmitting member 60 through the connecting joint 30. The power transmitting member 60 may be a rotary body such as, for example, a gear, or a longitudinal member such as, for example, a wire, a cable, a string, a rubber band, a spring, a belt, and a chain. The power transmitting member 60 may be bound or unbound by the driving module 40.

The connecting joint 30 may assist a motion of an ankle, for example, an ankle joint, that connects the first portion and the second portion of the user. The connecting joint 30 may be connected to the driving module 40 through the power transmitting member 60. The connecting joint 30 may assist a motion of stretching the ankle of the user when the power transmitting member 60 moves upward due to the driving module 40. Alternatively, the connecting joint 30 may assist a motion of bending the ankle of the user when the power transmitting member 60 moves downward.

Figure 3:
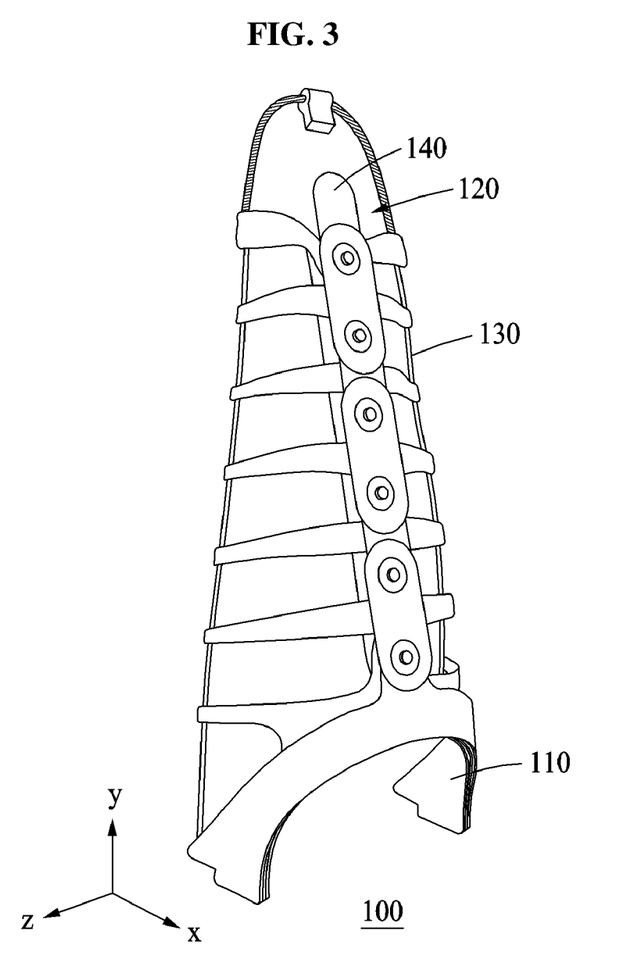
FIG. 3 is a perspective view illustrating a wearing module according to at least one example embodiment.

FIG. 3 is a perspective view illustrating the wearing module according to at least one example embodiment.

Referring to FIG. 3, the wearing module 100 includes a base frame 110 having a desired (or, alternatively, a predetermined) curved form to cover a body portion of a user, a middle frame 120 connected to the base frame 110 and having a longitudinal direction perpendicular to the base frame 110, and a connecting member 130 extended from both ends of the base frame 110 to cover an edge of the middle frame 120.

The wearing module 100 may further include a supporting member 140 disposed in the longitudinal direction of the middle frame 120 to support a pressure to be applied to the middle frame 120. The supporting member 140 may decrease a degree of deformation of the middle frame 120 when a force is applied to the wearing module 100 in an x axial direction.

The base frame 110 may be provided in a form of "U" and may substantially form a basic shape of the wearing module 100. When the base frame 110 is bendable, a supporting power of the wearing module 100 may be generally insufficient and thus, the base frame 110 may be formed by a rigid material, for example, a metal.

The middle frame 120 may be formed by a flexible material, for example, polypropylene (PP) and polyoxymethylene (POM) such that a form of the middle frame 120 may be changed based on a form of the base frame 110. The middle frame 120 may provide the supporting power with respect to a pressure applied in an x axial direction of the user, but the form of the middle frame 120 may be changed to a desired (or, alternatively, a predetermined) form in response to a body motion or a body change such that wearability for the user is enhanced.

The connecting member 130 may be formed by a material, for example, a wire or a fabric, which may bend in response to the change of the form of the middle frame 120. The connecting member 130 provided in a form of a wire and may cover the edge of the middle frame 120 to form an entire shape of the wearing module 100. The connecting member 130 provided in a form of a fabric may entirely cover the middle frame 120 including the edge of the middle frame 120.

The supporting member 140 may be fixed to the middle frame 120 along a center portion of the middle frame 120 extended in a Y axial direction. The supporting member 140 may prevent the middle frame 120 from being extensively bent in an X axial direction.

The supporting member 140 may include a plurality of separate parts, and neighboring parts among the separate parts may each be connected through a rolling joint and thus, each of the neighboring parts may correspondingly roll and rotate when the middle frame 120 is bent in a z axial direction.

Figure 4:
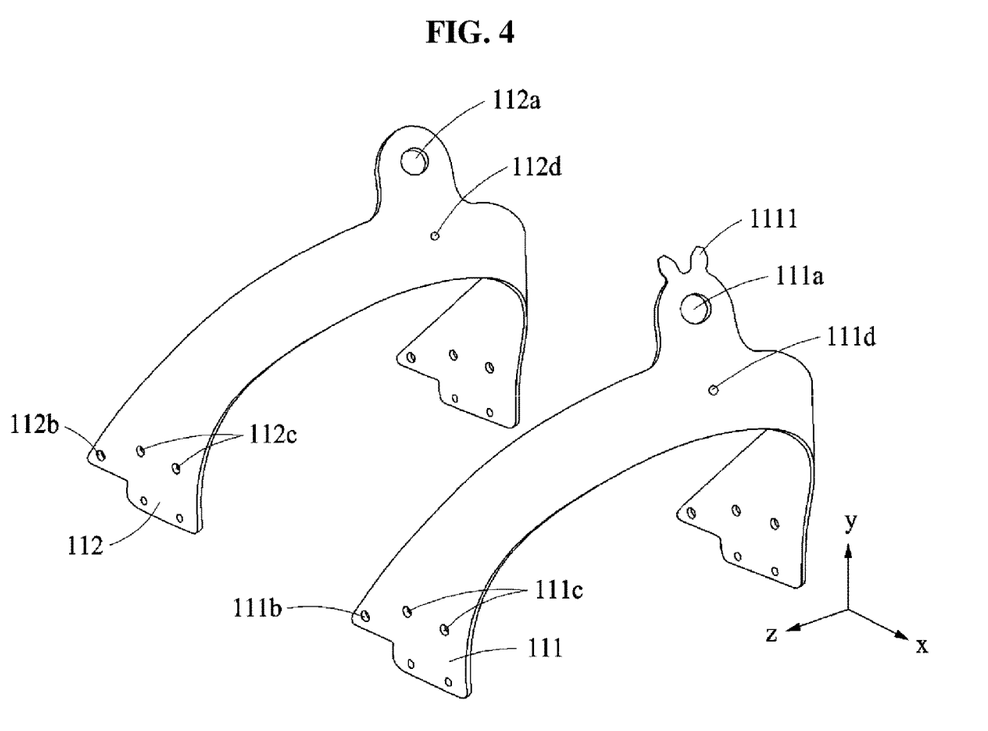
FIG. 4 is a perspective view of a base frame of a wearing module according to at least one example embodiment.

FIG. 4 is a perspective view of the base frame 110 of the wearing module 100 according to at least one example embodiment.

Referring to FIG. 4, both end portions of the base frame 110 may be flat, and the base frame 110 may be provided in an arched form. Both end portions of the base frame 110 provided in the arched form may be symmetrical based on a center of the base frame 110.

For example, the base frame 110 may include two pieces 111 and 112 each identical in size to the other. A bottom portion of the middle frame 120 may be disposed between the two pieces 111 and 112, and the two pieces 111 and 112 and the bottom portion of the middle frame 120 may be compressively attached through bolts that pass through the two pieces 111 and 112 and the bottom portion of the middle frame 120.

First holes 111a and 112a may be provided on a center portion of the two pieces 111 and 112 of the base frame 110 used to fix the middle frame 120 and the supporting member 140. In addition, gear teeth 1111 may be formed above the first hole 111a on the piece 111 of the base frame 110. The gear teeth 1111 may be connected to the supporting member 140.

Second holes 111b and 112b used to fix the connecting member 130 may be provided on both inner ends of outside end portions of the two pieces 111 and 112 of the base frame 110.

At least one third hole, for example, third holes 111c and 112c, to allow a bolt to pass through a bottom portion of the middle frame 120 and the two pieces 111 and 112 may be provided on both neighboring portions of the second holes 111b and 112b on both inner end portions of the two pieces 111 and 112 of the base frame 110.

Forth holes 111d and 112d to allow bolts pass through the bottom portion of the middle frame 120 and the two pieces 111 and 112 may be provided below the first holes 111a and 112a.

The second holes 111b and 112b through the fourth holes 111d and 112d may be symmetrically provided on both end portions of the two pieces 111 and 112 of the base frame 110.

Figure 5:
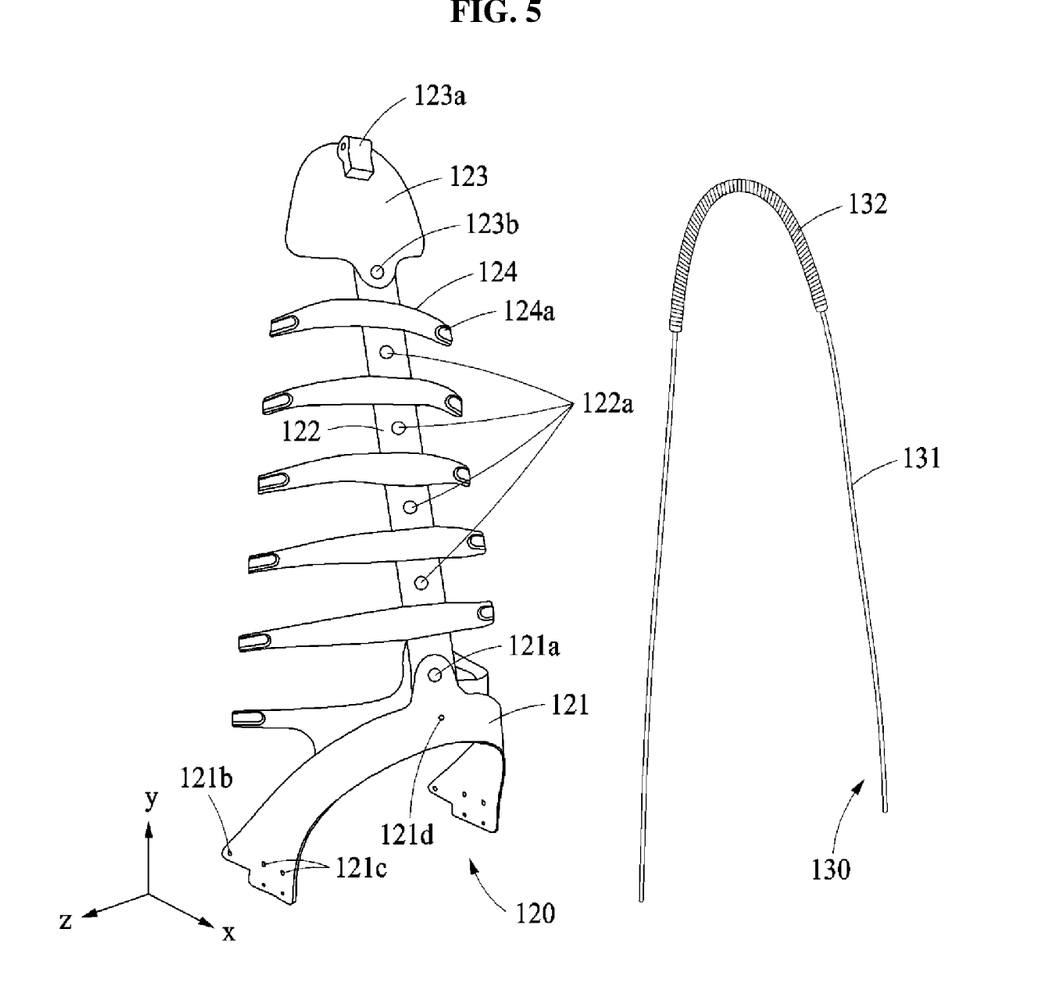
FIG. 5 is a perspective view of a middle frame and a connecting member of a wearing module according to at least one example embodiment.

FIG. 5 is a perspective view of the middle frame 120 and the connecting member 130 of the wearing module 100 according to at least one example embodiment.

Referring to FIG. 5, the middle frame 120 may be provided in a form of a fishbone. When each portion of the fishbone corresponds to each portion of the middle frame 120, a head of the fishbone corresponds to an upper portion 123, a backbone of the fishbone corresponds to a center portion 122, in which the supporting member 140 is configured to attach thereto, a rib of the fishbone corresponds to at least one arm 124, and a caudal fin of the fishbone corresponds to a bottom portion 121.

The middle frame 120 may further include the bottom portion 121 to be compressively attached between the two pieces 111, 112 of the base frame 110. The bottom portion 121 may have a size corresponding to a size of the base frame 110. The bottom portion 121 may have a form identical to a form of the base frame 110.

A bottom hole 121a may have a size at least substantially identical to a size of the first hole 111a and may be provided at a top of the bottom portion 121 such that the base frame 110 is connected to the supporting member 140 via a fastener inserted through the bottom hole 121a.

Holes 121b, 121c, and 121d corresponding to the second holes 111b and 112b, the third holes 111c and 112c, and the fourth holes 111d and 112d, respectively, of the two pieces 111 and 112 of the base frame 110 may be provided in a center and at both ends of the bottom portion 121.

The middle frame 120 may include the center portion 122 extended in a Y axial direction from the bottom portion 121, and a side portion extended in a perpendicular direction (Z axial direction) relative to a longitudinal direction of the center portion 122.

The side portion may include the at least one arm 124 symmetrically extended in a +Z axial direction and a −Z axial direction from the center portion 122. One end (or, alternatively, a middle) of the at least one arm 124 may be connected to the center portion 122. On another end of the at least one arm 124, a hole through which the connecting member 130 may pass may be formed or a passing member 124a may be provided.

A plurality of holes 122a may be provided on the center portion 122 through which bolts to fix the supporting member 140 may pass.

For example, the at least one arm 124 may have a tapered form of which a width is narrower from the center portion 122 to both ends of the at least one arm 124. When the at least one arm 124 has the tapered form, the connecting member 130 may smoothly move through a hole.

In addition, the middle frame 120 may include the upper portion 123 disposed on an uppermost end of the center portion 122. The upper portion 123 may have a half oval form.

At least one conduit tube member 123a may be disposed along an edge of the upper portion 123 such that the connecting member 130 passes through the conduit tube member 123a. The conduit tube member 123a may be disposed at the top of the upper portion 123 and at the corner of each side of the upper portion 123.

An upper hole 123b may be formed in a lower center of the upper portion 123 such that the supporting member 140 may be fixed.

The connecting member 130 may have a form of a wire and include a portion 132 having a relatively large diameter and a wire portion 131 having a relatively small diameter. The portion 132 may be a spring and pass through the conduit tube member 123a.

Figure 6:
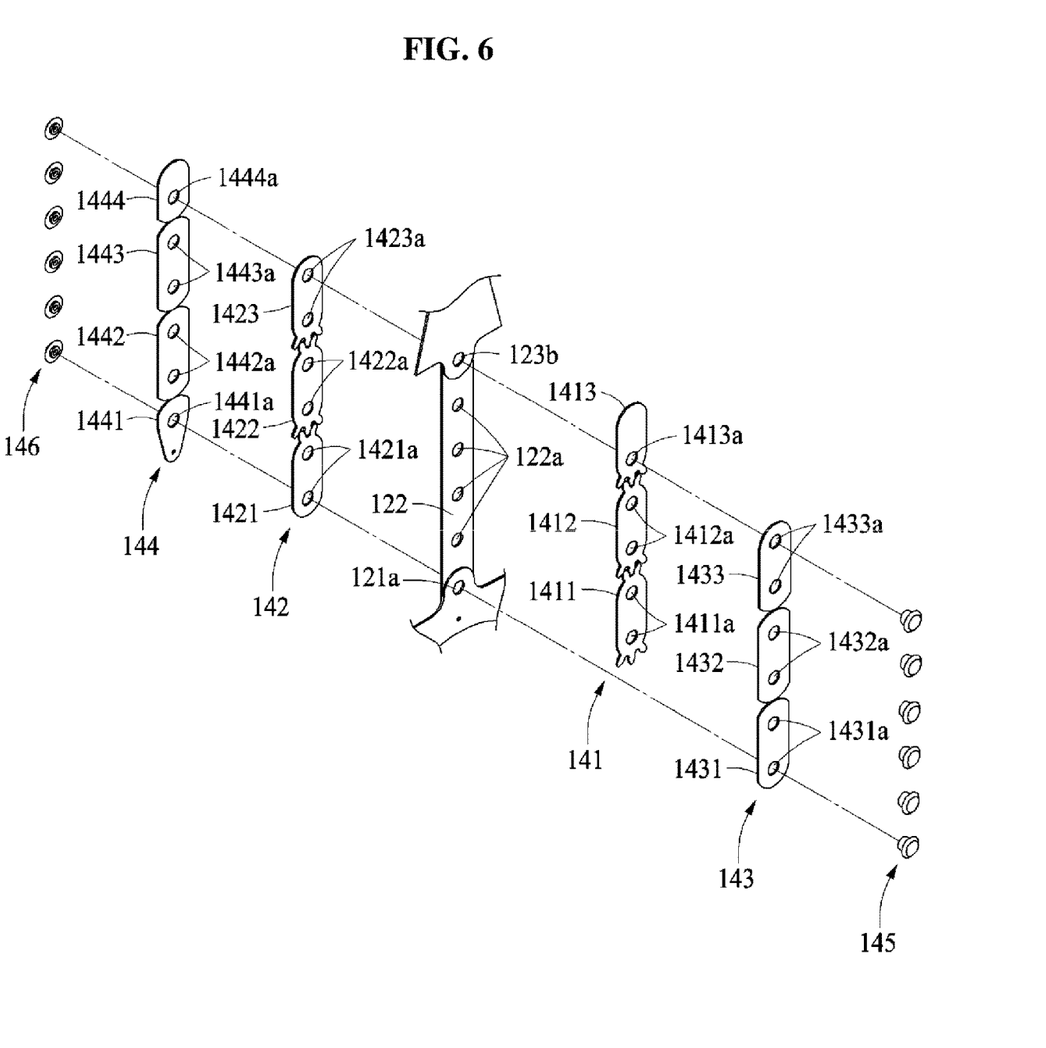
FIG. 6 is an exploded perspective view illustrating a supporting member of a wearing module according to at least one example embodiment.
Figure 7:
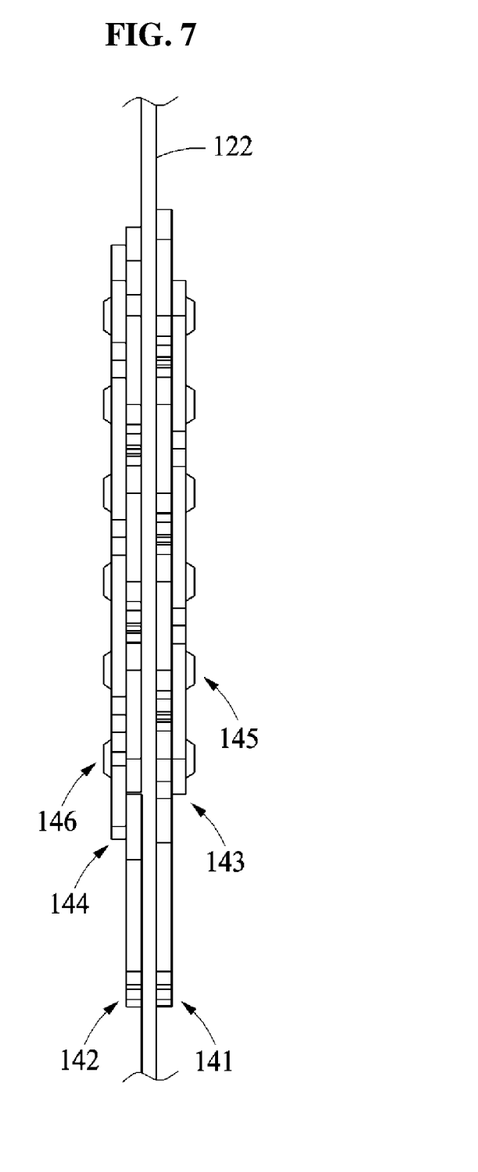
FIG. 7 is a side view of an assembly of a supporting member of a wearing module according to at least one example embodiment.

FIG. 6 is an exploded perspective view illustrating the supporting member 140 of the wearing module 100 according to at least one example embodiment, and FIG. 7 is a side view of an assembly of the supporting member 140 according to at least one example embodiment.

Referring to FIGS. 6 and 7, the supporting member 140 may include a first layer 141 including a plurality of sheets that are connected to each other through a rolling joint and a second layer 142 including a plurality of sheets that are connected to each other through a rolling joint. The second layer 142 is disposed on an opposite side of the first layer 141 based on the center portion 122.

In addition, the supporting member 140 may include a third layer 143 including a plurality of reinforcement sheets that are connected to each other through a rolling joint and a fourth layer 144 including a plurality of reinforcement sheets that are connected to each other through a rolling joint. The reinforcement sheets included in the third layer 143 connect neighboring end portions of the sheets included in the first layer 141 and the third layer 143 is disposed lateral to the first layer 141, and the reinforcement layers included in the fourth layer 144 connect neighboring end portions of the sheets included in the second layer 142 and the fourth layer 143 is disposed lateral to the second layer 142.

For example, the sheets included in each of the first layer 141, the second layer 142, the third layer 143, and the fourth layer 144 may be formed by a carbon fiber reinforcement plastic (CFRP) material that is light and flexible to a desired (or, alternatively, a predetermined) degree.

The first layer 141 includes a first sheet 1411, a second sheet 1412, and a third sheet 1413 that are disposed from bottom to top. The first sheet 1411, the second sheet 1412, and the third sheet 1413 may be attached to a front of the center portion 122 of the middle frame 120 by a bonding method using an adhesive.

The first sheet 1411 includes gear teeth on both end portions and two holes 1411a configured to connect the first layer 141 to another layer. The gear teeth at a lower end portion of the first sheet 1411 may be engaged with the gear teeth 1111 formed on the base frame 110.

The second sheet 1412 includes gear teeth on both end portions and two holes 1412a configured to connect the first layer 131 to another layer. One end portion of the second sheet 1412 is connected to one end portion of the first sheet 1411, and an opposite end portion of the second sheet 1412 is connected to one end portion of the third sheet 1413.

The third sheet 1413 includes gear teeth on a lower end portion such that the lower end portion of the third sheet 1413 is connected to the upper end portion of the second sheet 1412, and a hole 1413a configured to connect the first layer 141 to another layer. The hole 1413a may be disposed to correspond to the upper hole 123b formed on the upper portion 123 of the middle frame 120.

The second layer 142 includes a fourth sheet 1421, a fifth sheet 1422, and a sixth sheet 1423 that are disposed from bottom to top. The fourth sheet 1421, the fifth sheet 1422, and the sixth sheet 1423 may be attached to a back of the center portion 122 of the middle frame 120 by the bonding method using the adhesive.

The fourth sheet 1421 includes gear teeth on an upper end portion and two holes 1421a configured to connect the second layer 142 to another layer. A lower hole between the two holes 1421a is disposed to correspond to the bottom hole 121a formed on the base frame 110, and an upper hole between the two holes 1421a is disposed to correspond to a lower hole between the two holes 1411a of the first sheet 1411.

The fifth sheet 1422 includes gear teeth on both end portions and two holes 1422a configured to connect the second layer 142 to another layer. One end portion of the fifth sheet 1422 is connected to the upper end portion of the fourth sheet 1421 and an opposite end portion of the fifth sheet 1422 is connected to the lower end portion of the sixth sheet 1423. A lower hole between the two holes 1422a is disposed to correspond to the upper hole between the two holes 1411a of the first sheet 1411, and an upper hole between the two holes 1422a is disposed to correspond to the lower hole between the two holes 1412a of the second sheet 1412.

The sixth sheet 1423 includes gear teeth on a lower end portion such that the lower end portion of the sixth sheet 1423 is connected to the end portion of the fifth sheet 1422, and includes two holes 1423a configured to connect the second layer 142 to another layer. A lower hole between the two holes 1423a is disposed to correspond to an upper hole between the two holes 1412a of the second sheet 1412, and an upper hole between the two holes 1423a is disposed to correspond to the hole 1413a of the third sheet 1413.

The third layer 143 includes a seventh sheet 1431, an eighth sheet 1432, and a ninth sheet 1433 that are disposed from bottom to top. The third layer 143 may have a form identical to the form of the second layer 142, and gear teeth may not be formed on the third layer 143. The seventh sheet 1431, the eighth sheet 1432, and the ninth sheet 1433 may be disposed in front of the first layer 141.

Two holes 1431a formed on the seventh sheet 1431 may be disposed to correspond to the two holes 1421a formed on the fourth sheet 1421. Two holes 1432a formed on the eighth sheet 1432 may be disposed to correspond to the two holes 1422a formed on the fifth sheet 1422. Two holes 1433a formed on the ninth sheet 1433 may be disposed to correspond to the two holes 1423a formed on the sixth sheet 1423.

The fourth layer 144 includes a tenth sheet 1441, an eleventh sheet 1442, a twelfth sheet 1443, and a thirteenth sheet 1444 that are disposed from bottom to top. The fourth layer 144 may be disposed in back of the second layer 142.

The tenth sheet 1441 includes a hole 1441a, and the hole 1441a may be disposed to correspond to a lower hole between the two holes 1421a of the fourth sheet 1421.

The eleventh sheet 1442 includes two holes 1442a, and a lower hole between the two holes 1442a may be disposed to correspond to an upper hole between the two holes 1421a of the fourth sheet 1421, and an upper hole between the two holes 1442a may be disposed to correspond to a lower hole between the two holes 1422a of the fifth sheet 1422.

The twelfth sheet 1443 includes two holes 1443a, and a lower hole between the two holes 1443a may be disposed to correspond to the upper hole between the two holes 1422a, and an upper hole between the two holes 1443a may be disposed to correspond to the lower hole between the two holes 1423a of the sixth sheet 1423.

The thirteenth sheet 1444 includes a hole 1444a, and the hole 1444a may be disposed to correspond to the upper hole between the two holes 1423a of the sixth sheet 1423.

The supporting member 140 may include six bolts 145 and six corresponding nuts 146. However, example embodiments are not limited thereto. Each of the bolts 145 may pass through five holes disposed on a same axis. Each of the bolts 145 may sequentially pass through the third layer 143, the first layer 141, the holes 122a formed on the center portion 122, the second layer 142, and the fourth layer 144.

A diameter of the hole 122a is greater than a diameter of the bolt 145 and a diameter of each hole formed in layers is greater than the diameter of the bolt 145. Thus, the sheets of the layers 141 to 144 may rotate using each of the bolts as a rotation axis without restriction.

Figure 8:
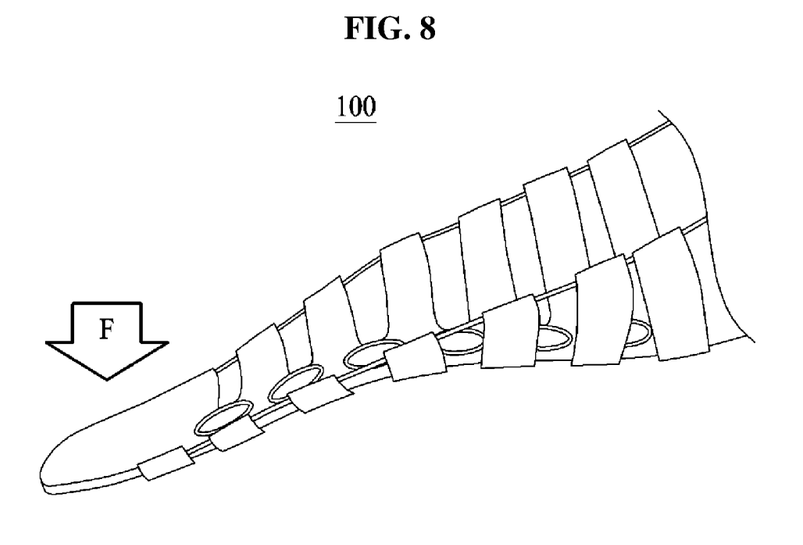
FIG. 8 is a perspective view of a wearing module to which a force is applied according to at least one example embodiment.
Figure 9:
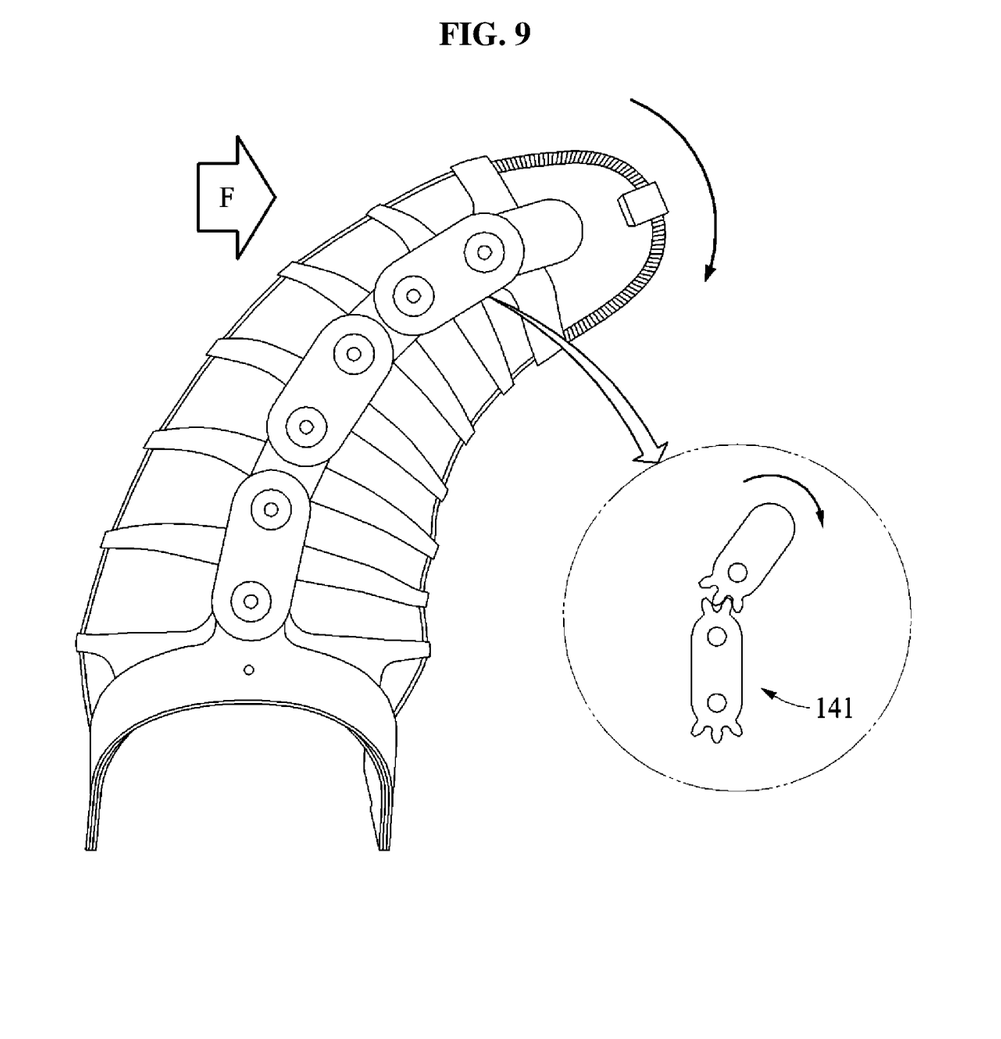
FIG. 9 is a perspective view of a wearing module bent in a lateral direction according to at least one example embodiment.

FIG. 8 is a perspective view of the wearing module 100 to which a force is applied according to at least one example embodiment, and FIG. 9 is a perspective view of the wearing module 100 bent in a lateral direction according to at least one example embodiment.

Referring to FIGS. 8 and 9, the wearing module 100 is adaptable to physical differences of users or differences in attachment positions. The wearing module 100 may autonomously change its structure to conform to a body structure.

Even when a force F is applied to the wearing module 100 as illustrated in FIG. 8, buckling may not occur due to the supporting member 140 even though a compressive force is applied to the middle frame 120.

From the view point of a sagittal plane of a user, the wearing module 100 may be well attached to a body of a user while the center portion 122 of the middle frame 120 endures the compressive force because the middle frame 120 is formed by a flexible material. From the view point of a frontal plane of a user, the wearing module 100 may also well adapt to a body structure of a wearer.

Compared to a supporting member that uses a single sheet layer, a resistance to buckling occurring when a compressive force is applied may be increased where the supporting member 140 uses at least two overlapping sheet layers.

In addition, when two neighboring sheets are bound in the supporting member 140 using a rolling joint, neighboring sheets may dependently move such that the supporting member 140 moves by maintaining equal angles between the neighboring sheets of the supporting member 140.

Figure 10A:
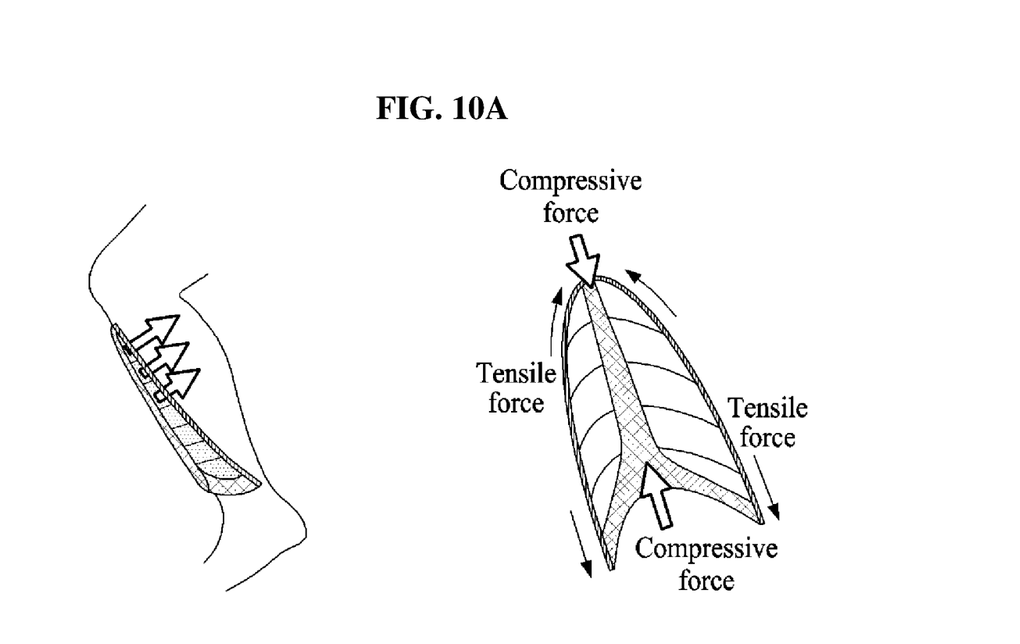
FIGS. 10A and 10B are diagrams illustrating a wearing module disposed on different portions of a user according to at least one example embodiment.
Figure 10B:
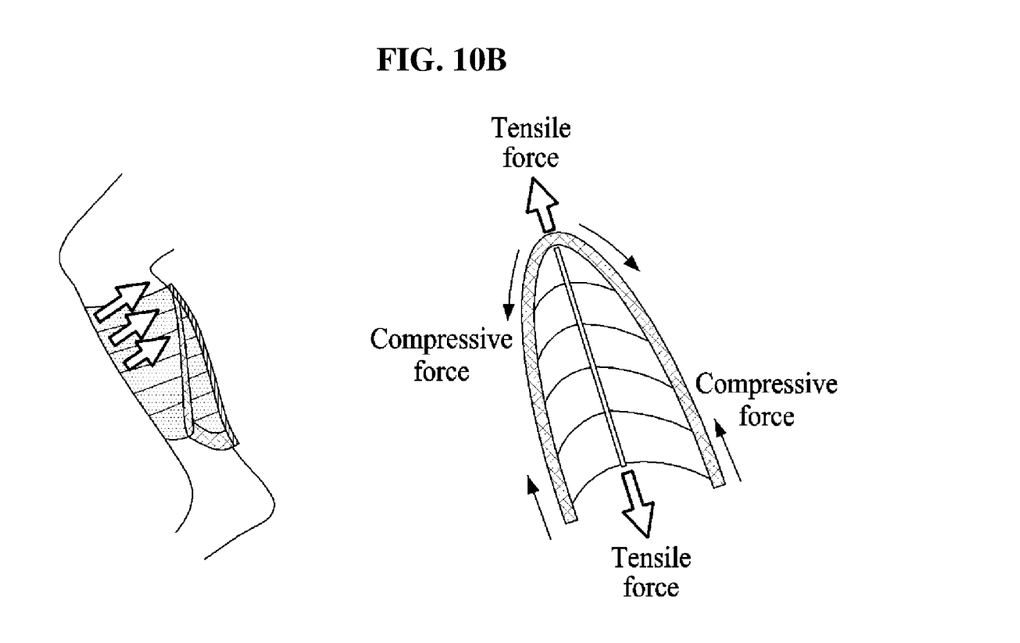

FIGS. 10A and 10B are diagrams illustrating the wearing module 100 disposed on different portions of a user according to at least one example embodiment.

FIG. 10A illustrates an example in which the user wears the wearing module 100 on a shin portion, and FIG. 10B illustrates an example in which the user wears the wearing module 100 on a calf portion.

Referring to FIG. 10A, when the user applies a force in a forward direction, the wearing module 100 may apply a supporting force in an opposite direction of the forward direction.

A compressive force may be applied to an upper portion and a center of a bottom portion of the middle frame 120, and a tensile force may be applied to a side portion of the middle frame 120. Thus, except for the base frame 100, an entire form of the wearing module 100 may be changed based on an application of the force.

Referring to FIG. 10B, when the user applies the force in the forward direction, the wearing module 100 may apply a force to pull a calf such that the wearing module 100 is prevented from being separated from the calf.

The tensile force may be applied to the upper portion and the center of the bottom portion of the middle frame 120, and the compressive force may be applied to the side portion of the middle frame 120. Thus, except for the base frame 110, the entire form of the wearing module 100 may be changed based on the application of the force.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A wearing module comprising:
    a base frame having a curved shape such that the base frame is configured to cover a body portion of a user, the base frame including a rigid material, the base frame including two end portions;
    a middle frame connected to the base frame and extending longitudinally in a first direction perpendicular to the base frame, the middle frame including a flexible material;
    a connecting member extending in the first direction from the end portions of the base frame and connected to edges of the middle frame, the connecting member configured to bend in response to a deformation of the middle frame caused by pressure applied thereto; and
    a supporting member extending in the first direction, the supporting member configured to support the middle frame in response to the pressure applied to the middle frame,
    wherein the supporting member includes a sheet layer including a plurality of sheets connected via a rolling joint.

2. The wearing module of claim 1, wherein the middle frame comprises:
    a center portion extending from the base frame in the first direction; and
    at least one side portion extending in a second direction perpendicular to the first direction.

3. The wearing module of claim 2, wherein the at least one side portion comprises:
    at least one arm connected in a middle thereof to the center portion such that the at least one arm symmetrically extends in the second direction from the center portion.

4. The wearing module of claim 3, wherein ends of the at least one arm have holes therein such that the connecting member passes through the holes.

5. The wearing module of claim 3, wherein the center portion includes at least one conduit tube member on an edge of an upper portion of the center portion such that the connecting member is configured to pass through the conduit tube member.

6. The wearing module of claim 1, wherein the base frame includes two pieces, and the middle frame further comprises:
a bottom portion configured to compressively attach to the base frame between the two pieces, the bottom portion having a size corresponding to a size of the two pieces of the base frame.

7. The wearing module of claim 1, wherein the supporting member further comprises:
a reinforcement sheet layer including a plurality of reinforcement sheets connected via the rolling joint, the reinforcement sheet layer configured to connect neighboring end portions of the plurality of sheets.

8. The wearing module of claim 7, wherein the sheet layer and the reinforcement sheet layer each include first layers and second layers, the first layers configured to attach to a front of the center portion and the second layers configured to attach to a back of the center portion.

9. A motion assistance apparatus comprising: a wearing module configured to cover a body portion of a user, the wearing module including, a base frame having a curved shape such that the base frame is configured to cover a body portion of a user, the base frame including a rigid material, the base frame including two end portions, a middle frame connected to the base frame and extending longitudinally in a first direction perpendicular to the base frame, the middle frame including a flexible material, a connecting member extending in the first direction from the end portions of the base frame and connected to edges of the middle frame configured to cover the middle frame, and to bend in response to a deformation of the middle frame caused by pressure applied thereto, and a supporting member extending in the first direction, the supporting member configured to support the middle frame in response to the pressure applied to the middle frame, the supporting member including a sheet layer including a plurality of sheets connected via a rolling joint; a supporting module configured to rotate relative to the wearing module; a driving module configured to drive the supporting module; and a power transmitting member configured to transmit a power to the supporting module.

10. The motion assistance apparatus of claim 9, wherein the connecting member includes a non-stretchable fabric.

11. The motion assistance apparatus of claim 9, wherein the supporting member is connected to the middle frame through a bolt such that the supporting member is rotatable with respect to the middle frame.

12. The motion assistance apparatus of claim 9, wherein the supporting member is configured to support the middle frame such that the middle frame is configured to bend less than a set amount in response to a motion transmitting pressure on the wearing module.

13. The motion assistance apparatus of claim 9, wherein the middle frame is configured to rotate, via the rolling joint, in response to rotation of the wearing module in a lateral direction.

* * * * *